United States Patent [19]

Turnbull et al.

[11] Patent Number: 5,185,353

[45] Date of Patent: Feb. 9, 1993

[54] 1,2 OXAZOLES USED FOR CONTROLLING NEMATODE PESTS

[75] Inventors: Michael D. Turnbull, Reading; Robert W. Parsons, Wokingham; Andrew D. S. Watkins, Crewe, all of England

[73] Assignee: Imperial Chemical Industries PLC, London, England

[21] Appl. No.: 610,891

[22] Filed: Nov. 8, 1990

[30] Foreign Application Priority Data

Nov. 14, 1989 [GB] United Kingdom ............... 8925739

[51] Int. Cl.$^5$ .................... A01N 43/82; A01N 43/76; A01N 43/80; C07D 261/06; C07D 263/34; C07D 271/12

[52] U.S. Cl. .................... 514/364; 514/374; 514/376; 514/377; 514/378; 548/247; 548/225; 548/226; 548/228; 548/230; 548/233; 548/235; 548/236; 548/131; 548/132; 548/133

[58] Field of Search ............. 548/247, 225, 226, 228, 548/230, 233, 235, 236, 131, 132, 133; 514/378, 374, 376, 377, 364

[56] References Cited

U.S. PATENT DOCUMENTS 3,781,438 12/1973 Gibbons .......................... 424/272
3,879,532 4/1975 Hass et al. ...................... 424/272
3,879,533 4/1975 Carr et al. ...................... 424/272

OTHER PUBLICATIONS

CA 107:198301t Preparation of ... acaricides. Mizukai et al., 1987, p. 763.
CA 72 79012y Nematocidal chloromethylisoxazoles. Mayer et al. p. 402, 1970.
CA 111 153697t An efficient ... heterocycles. Linderman et al. p. 712, 1989.
CA 115 92252c Preparation ... nematocides, Turnbull, p. 764, 1991.

Primary Examiner—Mary C. Lee
Assistant Examiner—Joseph K. McKane
Attorney, Agent, or Firm—Lynn Marcus-Wyner

[57] ABSTRACT

A method for killing or controlling nematode pests which comprises applying to the locus of the pests or to a plant susceptible to attack by the pest an effective amount of a compound of formula (I):

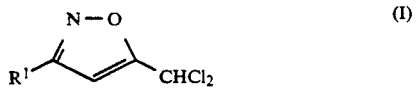

wherein $R^1$ is an optionally substituted aryl or optionally substituted heterocyclic group and novel compounds of formula (I) where $R^1$ is not phenyl.

10 Claims, No Drawings

1,2 OXAZOLES USED FOR CONTROLLING NEMATODE PESTS

The present invention relates to a method of killing or controlling nematodes and to novel isoxazole derivatives having nematicidal activity, processes for their preparation and compositions containing them.

According to the present invention there is provided a method of killing or controlling nematode pests which method comprises applying to the locus of the nematode pests or to a plant susceptible to nematode pests an effective amount of a compound of formula (I)

wherein $R^1$ is optionally substituted aryl or an optionally substituted heterocyclic group.

Compounds of formula (I) where $R^1$ is other than unsubstituted phenyl are novel and these compounds form a further aspect of the invention. Suitable aryl groups for $R^1$ include phenyl.

Suitable heterocyclic groups $R^1$ include a mono- or bicyclic ring structure having up to 10 atoms, up to 5 of which are selected from oxygen, nitrogen and sulphur. In particular the heterocyclic ring is an aromatic heterocyclic group.

Examples of such heterocyclic groups include furyl, thienyl, pyrryl, pyrazolyl, isothiazolyl, oxadiazolyl, thiodiazolyl, oxatriazolyl, dioxazolyl, oxathiazolyl, oxathiol, dioxinyl, pyridazinyl, pyrazinyl, piperazinyl, oxazinyl, isoxazinyl, oxathiazinyl, azepinyl, oxepinyl, thiepinyl, diazepinyl, benzofuranyl, isobenzofuranyl, benzothienyl, isobenzothienyl, indolyl, isoindolyl, indazolyl, indoleninyl, isobenzazolyl, isoindazolyl, indoxazinyl, benzoxazolyl, benzopyranyl, quinolinyl, isoquinolinyl, cinnolinyl, phthalazinyl, quinoxalinyl, quinazolinyl, naphthyridinyl, pyridopyridinyl, pyranyl, thiopyranyl, chromenyl, benzoxazinyl and benzisoxazinyl.

These heterocycles may be linked either through a carbon atom or when possible through a nitrogen atom.

Particular examples of heterocyclic groups $R^1$ include furyl, thiazolyl, pyrryl, benzfur-2-yl, naphth 1-yl, thiophen-2-yl, thiophen-3-yl, furan-3-yl, furan-2-yl, oxazol-2-yl or oxadiazol-5-yl.

Suitable optional substituents for the groups $R^1$ include one or more groups selected from oxo, mercapto, halo, such as fluoro, chloro, bromo or iodo, nitro, cyano, amino, mono or dialkylamino, amido optionally substituted with halo such as chloro, alkyl, alkenyl, alkynyl, cycloalkyl, haloalkyl such as trifluoromethyl, haloalkoxy such as trifluoromethoxy, optionally substituted aryl such as phenyl or naphthyl, hydroxy, alkoxy, alkoxycarbonyl, alkylcarbonyl, mono- or dialkylcarbamoyl, alkylthio, alkylsulphinyl, alkylsulphonyl, sulphonamido, alkylcarbonyloxy, alkylcarbonylamino optionally substituted with halogen, or heterocyclyl such as pyridyl and thienyl.

The substituents may be attached to a carbon and/or nitrogen atom of a heterocyclic group $R^1$.

In the above-mentioned list of substituents, the alkyl, alkenyl or alkynyl groups or moieties preferably contain from 1 to 6 carbon atoms. Suitable control substituents for the aryl groups include halo such as fluoro, chloro or bromo, $C_{1-6}$ alkyl or $C_{1-6}$ alkoxy.

Particular examples of substituents for $R^1$ include methyl, hydroxy, methoxy, ethoxy, fluoro, chloro, trifluoromethyl, cyano, methylsulphonyl, acetoxy or dichloroacetamido.

Preferred substituents are chloro, cyano and trifluoromethyl.

TABLE I

| CPD NO. | $R^1$ | CHARACTERISING DATA |
|---|---|---|
| 1 | phenyl | Melting Point: 63–64° C. |
| 2 | 3-chlorophenyl | Melting Point: 82–83° C. |
| 3 | 2-chlorophenyl | NMR: 6.8(s, 1H); 7.0(s, 1H); 7.4(m, 3H); 7.78(d, 1H) |
| 4 | 4-chlorophenyl | Melting Point: 76–77° C. |
| 5 | 4-ethoxyphenyl | NMR: 1.3(t, 3H); 5.0(m, 2H); 6.8(s, 2H); 6.95 (m, 2H); 7.70(m, 2H) |
| 6 | 4-cyanophenyl | NMR: 6.79(s, 1H); 6.82(s, 1H); 7.8(m, 4H) |
| 7 | 4-fluorophenyl | Melting Point: 81–82° C. |
| 8 | 4-trifluoromethylphenyl | Melting Point: 36–37° C. |
| 9 | 4-methoxyphenyl | Melting Point: 82–83° C. |
| 10 | 4-methylphenyl | Melting Point: 72–74° C. |
| 11 | 2,4-dichlorophenyl | NMR: 6.80(s, 1H); 7.02(s, 1H); 7.38(dd, 1H); 7.53(d, 1H); 7.72(d, 2H) |
| 12 | 4-acetoxyphenyl | Melting Point: 127–129° C. |
| 13 | 4-dichloroacetamidophenyl | NMR: 6.07(s, 1H); 6.78(s, 1H); 6.87(s, 1H); 7.72 (d, 2H); 7.85(d, 2H); 8.26(m, 1H) |
| 14 | 2-furyl | NMR: 6.55(d, 1H); 6.80(d, 2H); 6.95(d, 1H); 7.55(s, 1H) |
| 15 | 2-N-methylpyrryl | Melting Point: 57–58° C. |
| 16 | benzfur-2-yl | Melting Point: 138–139° C. |
| 17 | naphth-1-yl | NMR: 6.85,(d, 2H); 7.48, (m 3H); 7.70, (d, 1H); 7.95, (dd, 1H); 8.35, (dd, 1H) |
| 18 | thiophen-2-yl | NMR: 6.68(s, 1H); 6.80(s, 1H); 7.14S(m, 1H); 7.5(m, 2H) |
| 19 | 5-chlorothiophen-2-yl | Melting Point: 75–76° C. |
| 20 | 3-methylthiophen-2-yl | Melting Point: 65–66° C. |
| 21 | thiophen-3-yl | Melting Point: 66–67° C. |
| 22 | 4-methylthiophen-2-yl | NMR: 7.74(s, 2H); 7.05(s, 1H); 2.3(s, 3H); 7.33(s, 1H) |
| 23 | 5-methylthiophen-2-yl | NMR: 7.72, 7.73(2s, 2H); 6.8(d, 1H); 7.28(d, 1H) |
| 24 | furan-3-yl | Melting point: 57–58° C. |
| 25 | 5-methylfuran-2-yl | Melting Point: 56–57° C. |
| 26 | 4,5-dihydro-oxazol-2-yl | NMR: 4.0(t, 2H); 4.5 (t, 2H); 6.8(s, 1H); 6.9(s, 1H) |
| 27 | 3-i-propyloxadiazol-5-yl | NMR: 1.4(d, 6H); 3.2 (m, 1H); 6.8(s, 1H); 7.1(s, 1H) |

Preferably when $R^1$ is phenyl, it is substituted at the 4-position. Examples of the compounds of formula (I) are set out in Table I.

Compounds of formula (I) can be prepared by dehydrating a compound of formula (II):

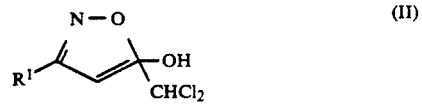

wherein $R^1$ is as defined in relation to formula (I). The dehydration can be carried out under conventional conditions, for example, using a dehydrating agent such as concentrated hydrochloric acid, trifluoroacetic acid or thionyl chloride. The dehydration is suitably carried out using excess dehydrating agent as solvent or in an inert organic solvent such as ethanol at elevated temperatures of from 40° C. to 75° C.

Compounds of formula (II) are suitably prepared by reacting a compound of formula (III):

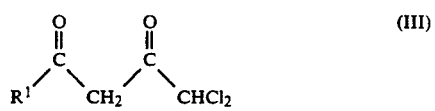

wherein $R^1$ is as defined in relation to formula (I); with hydroxylamine or a salt thereof in the presence of acid. The reaction is suitably carried out in an organic solvent such as lower alcohols, for example, ethanol. Preferably temperatures of from 10° C. to 30° C. are employed. The hydroxylamine is preferably in the form of an acid addition salt such as the hydrochloride salt which ensures that protons are present. The compound of formula (III) is suitably prepared by reacting a compound of formula (IV):

with a compound of formula (V):

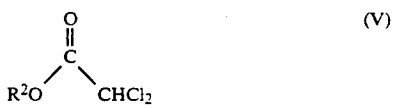

wherein $R^2$ is a $C_{1-6}$ alkyl group, such as methyl in the presence of a strong base.

Suitable strong bases for use in the reaction include sodium alkoxides such as sodium methoxide.

The reaction may be carried out in an inert organic solvent such as diethyl ether.

Compounds of formula (IV) and (V) are known compounds, or can be prepared from known compounds by standard methods. All the compounds of formula (I) can be prepared by analogy with the processes described herein and modification of side groups by conventional methods.

In order to apply the compound to the locus of the nematode, the compound is usually formulated into a composition which includes in addition to a compound of formula (I) suitable inert diluent or carrier materials, and/or surface active agents.

These compositions form a further aspect of the invention.

The compositions may also comprise another pesticidal material, for example, insecticide or acaricide, or a fungicide, or may also comprise an synergist, such as for example dodecyl imidazole, sesamax, safroxan, or piperonyl butoxide. The compositions may be in the form of dusting powders wherein the active ingredient is mixed with a solid diluent or carrier, for example, kaoline, bentonite, kieselguhr, or talc, or they may be in the form of granules, wherein the active ingredient is absorbed in as porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts or aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl, formamide, ethylene dichloride, isopropyl, alcohol, propylene glycol and other glycols, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 1.0% by weight of the active ingredient (approximately equivalent to from 5–20000 g/ha) is particularly useful.

In use the compositions are applied to the nematodes, to the locus of the nematodes, to the habitat of the nematodes, or to growing plants liable to infestation by the nematodes, by any of the known means of applying pesticidal compositions, for example, by dusting, spraying or incorporation of granules.

The compounds of the invention may be the sole active ingredient of the composition or they may be admixed with one or more additional active ingredients such as nematicides, insecticides, synergists, herbicides, fungicioes or plant growth regulators where appropriate. Suitable addition active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components. The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lambdacyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R, 3S)-2,2-dimethyl-3-(2-oxothiolan-3-ylidene- methyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fenofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avermectins or milbemycins, for example such as abamectin, avermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovolarvicides such as chlofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable synergists for use in the compositions have already been mentioned.

Suitable herbicides, fungicides and plant-growth regulators for inclusion in the compositions will depend upon the intended target and the effect required. An example of a rice selective herbicide which can be included is propanil, an example of a plant growth regulator for use in cotton is "Pix", for examples of fungicides for use in rice include blasticides such as blasticidin-S.

The ratio of the compound of the invention to the other active ingredient in the composition will depend upon a number of factors including type of target, effect required from the mixture, etc. However in general, the additional active ingredient of the composition will be applied at about the rate as it is usually employed, or at a slightly lower rate if synergism occurs.

The following Examples illustrate the invention. The compounds were identified and characterised by means of the melting points, nuclear magnetic resonance spectroscopy (NMR), or infra red spectroscopy.

EXAMPLE 1

This Example illustrates the preparation of Compound No. 1 of Table I.

Step a

Preparation of

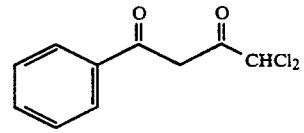

Acetophenone (10 g) and ethyldichloroacetate (13.0 g) in 30 ml of dry diethyl ether were added dropwise, with stirring to an ice/water cooled suspension of sodium powder in 40 ml of diethyl ether.

During the addition the mixture became dark brown in colour and after the addition the reaction mixture was allowed to warm to room temperature for one hour. After standing over a weekend the mixture was carefully acidified with 6N sulphuric acid. The two layers were then separated and the aqueous layer extracted twice with diethyl ether. All the ether extracts were combined, dried over MgSO$_4$, filtered and evaporated under reduced pressure to leave a dark oil.

The oil was purified by column chromatography through a silica column eluted with 60–80 petroleum ether/diethyl 4:1 which removed most of the brown colour.

Yield = 6.37 g (35%)

Step b

The 1,3-diketone from Step (a) (6.37 g) was dissolved in ethanol (30 ml) and added to hydroxylamine hydrochloride (2.0 g) in 3.5 ml of water. The resulting orange/brown solution was stirred at room temperature. After 2 hours concentrated hydrochloric acid (36 ml) in water (18 ml) was added and the mixture heated under reflux.

After 3 hours the reaction mixture was allowed to cool, quenched with water and extracted into diethyl ether.

The combined extracts were then washed with sodium bicarbonate solution, dried over MgSO$_4$, filtered and evaporated under reduced pressure to give a brown oil which solidified on standing. Compound No. 1 was separated from the oil using HPLC with 2% ethylacetate in hexane as the eluent, as a white crystalline solid.

Yield = 2.74 g $^1$H NMR δ (CDCl$_3$): 6.78 (s, 1H); 6.82 (s, 1H); 7.49 (m, 3H); 7.8 (m, 2H).

Melting point: 63°–64° C.

$^{13}$C (ppm) : 168.1, 162.6, 130.5, 129.0, 128.0, 126.8, 102.0, 59.9.

EXAMPLE 2

This Example illustrates the preparation of Compound No. 4 in Table 1.

Step a

Preparation of

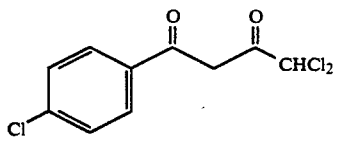

4-chloroacetophenone (10 g) and ethyldichloroacetate (10.1 g) as a solution in dry diethyl ether (15 ml) were added dropwise to a freshly prepared suspension of sodium methoxide in dry diethyl ether (100 ml). A dark red solution resulted during the addition which was left to stir for a further 4 hours.

The reaction was quenched with water (100 ml) and the two layers separated. The aqueous layer was extracted again with diethyl ether and the combined ether extracts were discarded.

The remaining aqueous layer was acidified with 2N HCl (100 ml) and extracted with ethyl acetate (2×50 ml).

The combined organic extracts were dried over MgSO$_4$, filtered and evaporated under reduced pressure to give a dark brown oil.

Yield=5.9 g (35%)

Step b

Preparation of

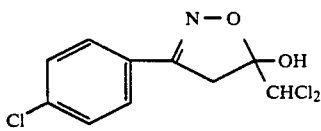

The product from Step (a) (5.9 g) as a solution in 25 ml of ethanol was stirred at room temperature while adding an aqueous solution of hydroxylamine hydrochloride (1.5 g) in 1 ml of water. The dark brown solution was left to stir for several hours before quenching with water. The aqueous product mixture was extracted with ethyl acetate and evaporated under reduced pressure to yield a brown oil.

Yield=5.7 g

The oil was subjected to column chromatography on silica eluting with hexane/ethylacetate/9:1 and the recovered desired hydrated isoxazole was triturated with hexane to give pale yellow crystals.

Yield=3.45 g (56%)

Step c

The isoxazole hydrate from Step (b) (3.45 g) as a solution in ethanol (18 ml) was stirred at room temperature while adding concentrated hydrochloric acid (6.5 ml). The orange solution that resulted was warmed under gentle reflux for 4 hours. The reaction mixture was allowed to cool and then poured into water and extracted with diethyl ether (2×50 ml). The combined ether extracts were washed with NaHCO3 solution and then dried over MgSO$_4$, filtration and evaporation under reduced pressure gave an orange oil. The oil was purified by column chromatography on silica, eluting with hexane/ethylacetate/9:1 to give 1 g of a crystalline solid. This solid was recrystallised from isopropyl alcohol to yield compound no. 4 as white needles.

Yield=800 mgs

Melting point: 76°-77° C. 1H NMR δ (CDCl$_3$): 6.8 (2s, 2H); 7.5 (m, 2H); 7.8 (m, 2H)

EXAMPLE 3

This example illustrates the preparation of Compound No. 12 in Table I.

Step a

Preparation of

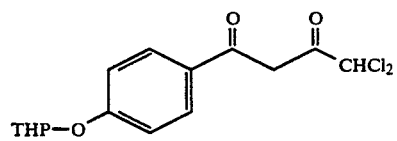

4-(Tetrahydropyran-2-yl)oxy-acetophenone (10 g) was added as a slurry in dry diethyl ether (50 ml) to sodium methoxide (4.91 g) suspended in dry diethyl ether (100 ml) and the mixture was stirred at ambient temperature for 10 minutes. A dark brown solution was formed to which was added methyldichloroacetate (6.5 g) in one portion and the reaction followed by gas chromatography. When the reaction was complete the solution was diluted with water (100 ml) and the aqueous layer (containing product) was separated. The ether portion was extracted with more water (100 ml) and aqueous sodium carbonate (2×100 ml of pH11). All aqueous layers were acidified with 2M HCl to pH7 and the product extracted into diethyl ether. The combined organic extracts were dried over magnesium sulphate, filtered and evaporated under reduced pressure to give an oil which was used without further purification in Step b.

Yield=4.86 g (31%)

Step b

Preparation of

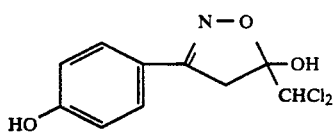

Hydroxylamine hydrochloride (0.99 g) in 8 ml of water was added over a period of 5 minutes to the diketone from Step (a) in ethanol (85ml). The homogeneous solution was stirred at ambient temperature for 30 minutes and then warmed to its reflux temperature until gas chromatography indicated that the reaction was complete. After cooling, solvent was removed by evaporation at reduced pressure to leave a brown oil. This oil was separated on a silica column eluted with hexane/ethyl acetate 1:1 to give a yellow oil which was triturated with chloroform, yielding a white solid. NMR and MS data indicated that it had the structure given above, loss of the protecting tetrahydropyranyl group having occurred.

Yield=1.26 g (34%)

Melting point: 154°-156° C. (decomposes)

¹H NMR δ (CDCl₃): 2.75 (s, 1H); 3.28 (d, 1H); 3.61 (d, 1H); 6.32 (s, 1H); 6.76 (d, 2H); 7.47 (d, 2H); 7.75 (s, 1H).

Step c

Preparation of

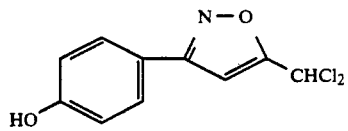

The isoxazole hydrate from Step (b) (0.788 g) was dissolved in trifluoroacetic acid (11 ml) and the mixture heated under reflux for 1 hour. The reaction was allowed to cool and the acid removed by evaporation under reduced pressure. The remaining brown oil was purified by chromatography using a silica column and ethyl actetate/petrol (b.pt. 40°-60° C.) (1:3) as eluent. The desired product was obtained as an off white solid.

Yield = 699 mg (95%)
Melting point: 104°-105° C.
¹H NMR δ (CDCl₃): 6.8 (d, 2H); 7.2 (s, 1H); 7.7 (d, 2H); 7.76 (s, 1H); 10.0 (s, 1H)

Step d

Preparation of compound no. 12 of Table 1.

The product from Step (c) (188 mg) was dissolved in acetic anhydride (12 ml) and warmed under gentle reflux for 70 minutes, at which time gas chromatography indicated that the reaction was complete. Excess acetic anhydride was removed by evaporation at reduced pressure, at a bath temperature of 65° C. The residual solid was dissolved in ethyl acetate (25 ml) and the organic layer washed with water (25 ml) and brine (25 ml). After drying over magnesium sulphate, the organic layer was concentrated at reduced pressure and the residue purified by chromatography using a silica column and ethyl actetate/petrol (b.pt. 40°-60° C.) (1:4) as eluent.

Yield = 197 mg (89%)
Melting point: 127°-129° C.
¹H NMR δ (CDCl₃): 1.34 (s, 3H); 6.78 (s, 1H); 6.85 (s, 1H); 7.24 (d, 2H); 7.82 (d, 2H)

EXAMPLE 4

This example illustrates the preparation of Compound No. 13 in Table I.

4-amino acetophenone (11.46 g) was added as a slurry in dry diethyl ether (60 ml) to sodium methoxide (9.17 g) suspended in dry diethyl ether (60 ml) and the mixture was stirred at ambient temperature for 5 minutes. Methyldichloroacetate (12.1 g) was then added over a period of 2 minutes. A yellow solid was deposited which was dissolved in water (100 ml) and the resulting yellow solution was extracted with diethyl ether (50 ml) to remove any starting material. The aqueous layer was brought to pH6 by addition of hydrochloric acid (2M) and extracted with diethyl ether (100 ml) and ethyl acetate (30 ml). The combined organic layers were dried over magnesium sulphate, filtered and evaporated under reduced pressure to give the diketone as a yellow solid (12.74 g). Hydroxylamine hydrochloride (5.4 g) in water (10 ml) was added to the intermediate diketone in ethanol (100 ml). The homogeneous solution was stirred at ambient temperature for 40 minutes and then warmed to its reflux temperature until gas chromatography indicated that the reaction was complete. After cooling, solvent was removed by evaporation at reduced pressure and the residue was partitioned between ethyl acetate (100 ml) and water (100 ml). The organic layer was washed with water (50 ml) and brine (50 ml) and dried over magnesium sulphate. Solvent was removed by evaporation at low pressure to yield a yellow solid which thin layer chromatography indicated to be a mixture. The solid (8 g) was dissolved in trifluoroacetic acid (70 ml) and the mixture heated under reflux for 70 minutes. The reaction was allowed to cool and the acid removed by evaporation under reduced pressure. The remaining yellow-brown solid was separated into its components by chromatography using a silica column eluted with ethyl acetate/hexane (1:3) to give compound 13 as one pure fraction.

Yield = 300 mg (1% over 3 steps)
¹H NMR δ (CDCl₃): 6.07 (s, 1H); 6.78 (s, 1H); 6.87 (s, 1H); 7.72 (d, 2H); 7.85 (d, 2H); 8.26 (m, 1H)

EXAMPLE 5

This Example illustrates the preparation of Compound No. 14 in Table I.

Step a

Preparation of

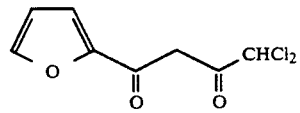

2-Acetylfuran (10 g) was added in one portion to a stirred suspension of fresh sodium methoxide (4.9 g) in dry diethyl ether (100 ml). A dark red solution resulted which was stirred for ½ hour before adding methyldichloroacetate (13 g) in one portion (slight exotherm) and the reaction was followed by gas chromatography. When the reaction was complete the dark red solution was diluted with water (100 ml), acidified with 2N hydrochloric acid and then extracted with ether (x 3), the combined organic extracts were dried over MgSO₄, filtered and evaporated under reduced pressure to give a black oil. The oil was distilled under vacuum to give a brown oil.

Yield = 9.5 g (48%)
Boiling point: 92°-93° C./0.1 mbar.

Step b

Preparation of

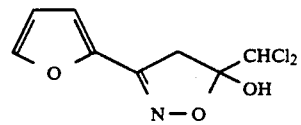

Hydroxylamine hydrochloride (3 g) in 10 mls of water was added in one portion to a stirred solution of the diketone from Step (a) in ethanol (100 ml). The homogeneous solution was allowed to stand at ambient temperature overnight. The solution was evaporated under reduced pressure to remove excess ethanol and the remaining residue was diluted with water (100 ml). The aqueous product mixture was extracted with ethylacetate (x 2). The combined extracts were dried over MgSO₄, filtered and evaporated under reduced pressure to an orange oil. This oil was separated on a silica column eluted with hexane/ethylacetate/3:1 to give the desired product.

Yield = 3.3 g (33%)
Melting point 106°-107° C.
¹H NMR δ (CDCl₃): 3.5 (d, 1H); 3.7 (d, 1H); 3.9 (s, 1H); 5.9 (s, 1H); 6.5 (d, 1H); 6.8 (d, 1H); 7.5 (s, 1H).

Step c

The isoxazole hydrate from Step (b) (3 g) as a solution in ethanol (50 ml) was vigorously stirred while adding concentrated hydrochloric acid (10 ml) in one portion. The reaction mixture was warmed under gentle reflux for 2 days. On cooling, the reaction mixture was quenched with water (100 ml), and extracted with 3 portions of ethyl acetate. The combined organic extracts were dried over MgSO₄ and evaporated under reduced pressure to a brown oil. Brown oil was purified using column chromatography on silica eluting with hexane/ethyl acetate/3:1 to give compound no. 14 as a colourless oil.

¹H NMR δ (CDCl₃): 6.55 (d, 1H); 6.80 (d, 2H); 6.95 (d, 1H); 7.55 (s, 1H).

EXAMPLE 6

This Example illustrates the preparation of Compound No. 11 in Table I.

2,4-Dichloroacetophenone (15.3 g) was converted to the appropriate isoxazole hydrate as described in Example 1 Steps (a) and (b). This compound (1.49) was dissolved in an excess of trifluoroacetic acid and heated under reflux for ca. one hour after which time the reaction mixture was evaporated under reduced pressure to remove the excess trifluoroacetic acid leaving a brown oil. This oil was diluted with diethyl ether, washed with water (2×5 ml) and the organic layer separated and dried over MgSO₄. Filtration and evaporation gave a brown oil which was purified by chromatography using a silica column and hexane/ethyl acetate (9:1) as eluent. The desired product was obtained as an orange oil (420 mg).

EXAMPLE 7

This Example illustrates the preparation of Compound Nos. 26 and 27 of Table I.

Step a

Preparation of

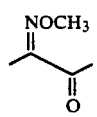

2,3-Butanedione monoxime (100 g) in 250 ml of acetone was added to a stirred suspension of potassium carbonate (136 g) in 600 ml of acetone. During the addition the suspension became yellow in colour and after the addition the suspension was stirred for one hour. Dimethyl sulphate (124 g) was then added dropwise at a rate such that the resultant exotherm did not exceed 35° C. A creamy white suspension resulted which was stirred for 2 hours and then warmed to gently reflux for a further 2 hours. The reaction mixture was allowed to cool before filtering. The excess acetone was distilled out using a fractionating column leaving a pale brown oil. This oil was distilled under partial vacuum to give a pale yellow oil.

Yield = 94 g (82%)
Boiling Point 58°-60° C. at 93 mm Hg
¹H NMR δ (CDCl₃) 1.9 (s, 3H); 2.35 (s, 3H); 4.1 (s, 3H)

Step b

Preparation of

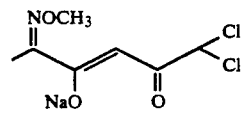

The product from step a (94 g) and methyldichloroacetate (117 g) were added as a mixture to a stirred suspension of sodium methoxide (49 g) in 750 ml of dry diethylether. Exotherm was controlled with an ice/water bath. During the addition a brown solution resulted and after the addition this changed to a yellow precipitate. The precipitate was filtered and washed with ether (250 ml) and the filter cake was allowed to air dry.

Yield = 114.2 g (59%)

Step c

Preparation of

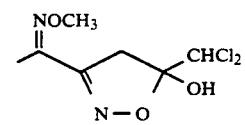

The product from step b (114.2 g) was dissolved in ethanol (1200 ml) and a solution of hydroxylamine hydrochloride (32 g in 100 ml) was added dropwise over 1 hour. After the addition the reaction mixture was left to stir overnight. The reaction was then filtered and the filtrate was evaporated under reduced pressure to give a yellow solid. This solid was recrystallised from hexane to give yellow crystals.

Yield = 73 g (66%)
¹H NMR δ (CDCl₃): 2.1 (s, 3H); 3.4 (q, 2H); 3.6 (s, 1H); 4.0 (s, 3H); 5.9 (s, 1H)

Step d

Preparation of

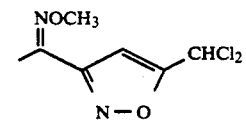

The product from step c (71 g) was dissolved in thionyl chloride (100 ml) and the reaction mixture was heated to gentle reflux for 2 hours. The reaction was allowed to cool before removing the excess thionyl chloride under reduced pressure. The remaining orange oil was distilled under high vacuum to yield a pale yellow oil (boiling point 58°-68° C. at 0.05 mmHg). The oil was crystallised from 40/60 petrol ether at low temperature to give colourless needles.

Yield = 47 g (72%)
¹H NMR δ (CDCl₃): 2.25 (s, 3H); 4.0 (s, 3H); 6.7 (s, 1H); 6.9 (s, 1H)

Step e

Preparation of

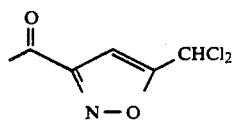

The product from step d (37 g) was added to a mixture of levulinic acid (50 ml) and concentrated hydrochloric acid (50 ml) and the reaction mixture was warmed to 90° C. for 6 hours. The reaction was allowed to cool and was then poured onto solid sodium bicarbonate. Once the carbon dioxide had been evolved, the resultant slurry was diluted with water (200 ml) and then filtered. The filtrate was extracted with diethyl ether (3 times) and the combined organic extracts were dried over anhydrous magnesium sulphate, filtered and evaporated under reduced pressure to yield a brown oil. The oil was distilled in a kugelrohr distillation apparatus to give a colourless oil (boiling point: 60°-62° C. at 0.05 mmHg).

Yield=22 g (69%)

$^1$H NMR δ (CDCl$_3$) 2.7 (s, 3H); 6.8 (s, 1H); 6.9 (s, 1H)

Step f

Preparation of

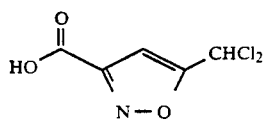

The product from step e (10 g) was added in one portion to a stirred solution of potassium dichromate (44 g) in 300 ml of 2N sulphuric acid. The mixture was warmed to 80° C. for 6 hours. During this time the colour changed from orange to green. The resultant green solution was cooled and then extracted several times with ethyl acetate. The combined organic extracts were washed several times with sodium bicarbonate and then discarded. The combined aqueous extracts were re-acidified with 2N hydrochloric acid and then extracted several times with ethyl acetate. The combined organic extracts were dried over anhydrous magnesium sulphate, filtered and the solvent removed under reduced pressure to give a pale green solid.

Yield=7.68 g (76%)

Step g

Preparation of

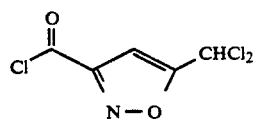

The product from step f (7.68 g) was dissolved in thionyl chloride (15 ml) containing one drop of dimethyl formamide, and the mixture was refluxed for 3 hours. The excess thionyl chloride was removed under reduced pressure to give a purple oil. This oil was dissolved in 20 ml of ether and the resultant suspension was filtered and the filtrate evaporated to give an orange oil.

Yield=5.98 g (71%)

Step h

Preparation of

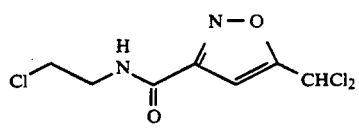

The product from step g (1.5 g) was added to a solution of ethanolamine 0.87 g in dichloromethane at 0° C. After the addition the solution was stirred at room temperature for 1 hour. The reaction was quenched with water and the dichloromethane layer separated. The aqueous layer was extracted several times with dichloromethane before discarding. The combined organic extracts were dried over anhydrous MgSO$_4$, filtered and the solvent removed to give a yellow oil ( Yield=1.16 g (75%)).

The oil was dissolved in thionyl chloride and stirred at room temperature for 2 hours, and then warmed to reflux for 1 hour. The excess thionyl chloride was removed under reduced pressure to give a yellow oil. The oil was taken up in ether and washed several times with saturated sodium bicarbonate solution. The ether extracts were dried over anhydrous magnesium sulphate, filtered and the solvent removed to give a pale yellow solid ( Yield=1.10 g (92%)).

The solid was recrystallised from hexane/ethyl acetate to give beige needles.

Yield=980 mg (82%)

Step i

Preparation of Compound No 26 of Table I.

The product from step h (0.8 g) in 15 ml of dry dimethylformamide and potassium carbonate (0.43 g) were heated together at 80° C. for 24 hours. The solution was then quenched into saturated brine solution and extracted several times with ether (3×50 ml). The combined organic extracts were dried over anydrous magnesium sulphate, filtered and the solvent removed under reduced pressure to form a yellow solid. The solid was recrystallised from hexane/diethylether to give yellow crystals.

Yield=430 mg (63%)

Step j

Preparation of Compound No 27 of Table I.

The product from step g (0.5 g) was added to a solution of isopropylamidoxime (0.25 g) in 10 ml of toluene. A white precipitate resulted followed by an exotherm of 22° to 35° C. After the addition, the suspension was heated to reflux for 2 hours. The reaction mixture was then cooled and quenched with water (60 ml) and extracted several times with ethyl acetate. The combined organic extracts were washed with saturated sodium bicarbonate and dried over anhydrous magnesium sulphate. Filtration and solvent removal under reduced pressure gave an orange oil. The oil was purified by column chromatography through silica gel eluting with hexane/ether (8:1) to give a colourless oil.

Yield=270 mg (45%)

EXAMPLE 8

In order to illustrate the nematicidal properties of the compounds of formula (I), tomato plants (6-8 weeks old, variety 'Moneymaker') were planted out into soil infested with root-knot nematodes (*Meloidogyne incognita*) and the soil drenched with a composition of the compound of formula (I) (obtained by diluting one part of a solution of the compound in a 1:1 mixture of acetone and ethanol with 99 parts of water containing 1% of a wetting agent) at a rate of 200 ml/kg of soil. The roots of the plants were examined after 3 weeks to determine the % reduction in the number of root knots as compared with a similar treatment omitting the compound. The results are given in Table II.

TABLE II

| COMPOUND NO. | RATE OF APPLICATION PPM | % ROOT KNOT REDUCTION |
|---|---|---|
| 1 | 10 | 78 |
| 2 | 5 | 34 |
| 3 | 5 | 41 |
| 4 | 5 | 81 |
| 5 | 1 | 22 |
| 6 | 5 | 78 |
| 7 | 2.5 | 29 |
| 8 | 2.5 | 40 |
| 9 | 2.5 | 59 |
| 10 | 2.5 | 21 |
| 11 | 5 | 38 |
| 12 | 2.5 | 51 |
| 13 | 5 | 49 |
| 14 | 2 | 88 |
| 15 | 2 | 43 |
| 16 | 2.4 | 43 |
| 17 | 2.5 | 50 |
| 18 | 2.5 | 17 |
| 19 | 2.5 | 77 |
| 20 | 2.5 | 60 |
| 21 | 2.5 | 74 |
| 22 | 2.5 | 52 |
| 23 | 2.5 | 81 |
| 24 | 2.5 | 95 |
| 25 | 2.5 | 91 |
| 26 | 2.5 | 53 |
| 27 | 5 | 96 |

The following examples demonstrate formulations suitable for applying the compounds of the present invention. The amount of ingredient is expressed in parts by weight or grams per liter as indicated.

EXAMPLE 9

This example demonstrates granules suitable for soil application. The granules can be made be standard techniques such as impregnation, coating, extrusion or agglomeration.

| Impregnated granule: | Active ingredient | 5 |
|---|---|---|
| | Wood Rosin | 2.5 |
| | Gypsum granules (20-40 mesh) | 92.5 |
| Coated granule: | Active ingredient | 5 |
| | Solvesso* 200 | 4 |
| | Calcium carbonate granules (30-60 mesh) | 91 |
| Slow release granule: | Active ingredient | 10 |
| | Polyvinylacetate/vinyl chloride copolymer latex | 5 |
| | Attapulgus granules | 85 |

Example 10

This example demonstrates formulations for use as a spray. The compounds can be formulated as wettable powders, water dispersible granules, emulsifiable concentrates, emulsions or microcapsule suspensions for application diluted in water.

| Emuslifiable concentrate: | Active ingredient | 250 |
|---|---|---|
| | Calcium dodecyl benzene sulphonate | 50 |
| | Nonyl phenol ethoxylate | 50 |
| | Alkylbenzene solvent | to 1 liter |
| Wettable powder: | Active ingredient | 45 |
| | lignosulphonate dispersant | 5 |
| | silica | 25 |
| | sodium lauryl sulphate | 20 |
| | china clay (kaolin) | 5 |
| Microcapsule suspension: | Active ingredient | 250 |
| | toluene diisocyanate | 10 |
| | polymethylene polyphenyl isocyanate | 20 |
| | nonyl phenol ethoxylate | 6 |
| | lignosulphonate dispersant | 15 |
| | xanthan gum | 1 |
| | bentonite | 10 |
| | biocide 'Proxel'* | 0.1 |
| | sodium carbonate | 5 |
| | water | to 1 liter |

The microcapsule suspensions can be used as a spray, soil drench or as an intermdiate to prepare slow release granules for application to the soil.

We claim:

1. A method for killing or controlling nematode pests which comprises applying to the locus of the pests or to a plant susceptible to attack by the pest an effective amount of a compound of formula (I):

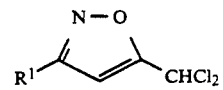

wherein $R^1$ is selected from the group, phenyl, substituted phenyl, furyl, substituted furyl, pyrryl, substituted pyrryl, benzfur-2-yl, substituted benzfur-2-yl, naphth-1-yl, substituted naphth-1-yl, furan-2-yl, substituted furan-2-yl, furan-3-yl, substituted furan-3-yl, thiophen-2-yl, substituted thiophen-2-yl, thiophen-3-yl, substituted thiophen-3-yl, oxazol-2-yl, substituted oxazol-2-yl, 4,5dihyro-oxazol-2-yl, substituted 4,5dihydro-oxazol-2-yl, oxadiazol-5-yl and substituted oxadiazol-5-yl wherein the substituents of $R^1$ are one or more substituents selected from the group halo, hydroxy, $C_1$-$C_6$ alkyl, $C_1$-$C_6$ alkylthio, $C_1$-$C_6$ alkoxy, cyano, acetoxy, $C_1$-$C_6$ haloalkyl, $C_1$-$C_6$ alkylcarbonyloxy, $C_1$-$C_6$ alkylsulphonyl and $C_1$-$C_6$ alkylcarbonylamino wherein the $C_1$-$C_6$ alkylcarbonylamino can be substituted with halogen.

2. A method according to claim 1 wherein $R^1$ is phenyl 3-chlorophenyl, 2-chlorophenyl, 4-chlorophenyl, 4-ethoxyphenyl, 4-cyanophenyl, 4-fluorophenyl, 4-trifluoromethylphenyl, 4-methoxyphenyl, 4-methylphenyl, 2,4-dichlorophenyl, 4-acetoxyphenyl or 4-dichloroacetamidophenyl.

3. A method according to claim 1 wherein $R^1$ is 2-furyl, 2-N-methylpyrryl, benzfur-2-yl, thiophen-2-yl, 5-chlorothiophen-2-yl, 3-methyl-2-yl, thiopheny-3-yl, 4-methylthiophen-2-yl, 5methylthiophen-2-yl, furan-3-yl, 5-methylfuran-2-yl, 4,5-dihydro-oxazol-2-yl, or 3-i-propyloxadiazol-5-yl.

4. A nematocidal composition comprising an effective amount of a compound of formula (I).

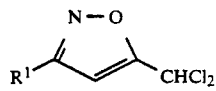

(I)

wherein R¹ is selected from the group, phenyl, substituted phenyl, furyl, substituted furyl, pyrryl, substituted pyrryl, benzfur-2-yl, substituted benzfur-2-yl, naphth-1-yl, substituted naphth-1-yl, furan-2-yl, substituted furan-2-yl, furan-3-yl, substituted furan-3-yl, thiophen-2-yl, substituted thiophen-2-yl, thiophen-3-yl, substituted thiophen-3-yl, oxazol-2-yl, substituted oxazol-2-yl, 4,5dihydro-oxazol-2-yl, substituted 4,5dihydro-oxazol-2-yl, oxadiazol-5-yl and substituted oxadiazol-5-yl wherein the substituents of R¹ are one or more substituents selected from the group halo, hydroxy, $C_1$–$C_6$ alkyl, $C_1$–$C_6$ alkylthio, $C_1$–$C_6$ alkoxy, cyano, acetoxy, $C_1$–$C_6$ haloalkyl, $C_1$–$C_6$ alkylcarbonyloxy, $C_1$–$C_6$ alkylsulphonyl and $C_1$–$C_6$ alkylcarbonylamino wherein the $C_1$–$C_6$ alkylcarbonylamino can be substituted with halogen.

5. A compound of formula I.

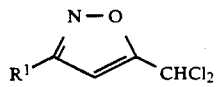

(I)

wherein R¹ is selected from the group, phenyl, substituted phenyl, furyl, substituted furyl, pyrryl, substituted pyrryl, benzfur-2-yl, substituted benzfur-2-yl, naphth-1-yl, substituted naphth-1-yl, furan-2-yl, substituted furan-2-yl, furan-3-yl, substituted furan-3-yl, thiophen-2-yl, substituted thiophen-2-yl, thiophen-3-yl, substituted thiophen-3-yl, oxazol-2-yl, substituted oxazol-2-yl, 4,5dihydro-oxazol-2-yl, substituted 4,5dihydro-oxazol-2-yl, oxadiazol-5-yl and substituted oxadiazol-5-yl wherein the substituents of R¹ are one or more substituents selected from the group halo, hydroxy, $C_1$–$C_6$ alkyl, $C_1$–$C_6$ alkylthio, $C_1$–$C_6$ alkoxy, cyano, acetoxy, $C_1$–$C_6$ haloalkyl, $C_1$–$C_6$ alkylcarbonyloxy, $C_1$–$C_6$ alkylsulphonyl and $C_1$–$C_6$ alkylcarbonylamino wherein the $C_1$–$C_6$ alkylcarbonylamino can be substituted with halogen.

6. A compound

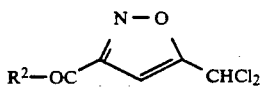

wherein R² is OH or $CH_3$.

7. A method according to claim 1 wherein R¹ is furyl, benzfur-2-yl, furan-3-yl, furan-2-yl, substituted furyl, substituted benzfur-2yl, substituted furan-3-yl, and substituted furan-2-yl,; wherein one or more substituents are selected from the group $C_1$–$C_3$ alkyl; $C_1$–$C_3$ alkoxy; hydroxy; halo; cyano; $C_1$–$C_3$ haloalkyl, acetoxy, $C_1$–$C_3$ alkylsulphonyl, and haloacetamido.

8. A nematocidal composition according to claim 4 wherein R¹ is 2-furyl, benzfur-2-yl, furan-3-yl, or 5-methylfuran-2-yl.

9. A nematocidal composition according to claim 8 wherein R¹ is 2-furyl; furan-3-yl; and 5-methyl furan-2-yl.

10. A compound according to claim 5 wherein R¹ is 2-furyl; furan-3-yl; and 5-methyl furan-2-yl.

* * * * *